(12) United States Patent
Shadduck

(10) Patent No.: US 7,678,120 B2
(45) Date of Patent: *Mar. 16, 2010

(54) INSTRUMENTS AND TECHNIQUES FOR CONTROLLED REMOVAL OF EPIDERMAL LAYERS

(75) Inventor: John H. Shadduck, Tiburon, CA (US)

(73) Assignee: Axia MedSciences, LLC, Tiburon, CA (US)

( * ) Notice: Subject to any disclaimer, the term of this patent is extended or adjusted under 35 U.S.C. 154(b) by 104 days.

This patent is subject to a terminal disclaimer.

(21) Appl. No.: 11/417,396

(22) Filed: May 3, 2006

(65) Prior Publication Data

US 2006/0200172 A1  Sep. 7, 2006

Related U.S. Application Data

(63) Continuation of application No. 10/699,747, filed on Nov. 3, 2003, which is a continuation of application No. 09/648,025, filed on Aug. 25, 2000, now Pat. No. 6,641,591.

(60) Provisional application No. 60/150,782, filed on Aug. 26, 1999.

(51) Int. Cl.
A61B 17/50 (2006.01)
A61M 35/00 (2006.01)

(52) U.S. Cl. .................. 606/131; 606/132; 604/289

(58) Field of Classification Search .......... 606/131, 606/132, 133; 604/289, 313, 315
See application file for complete search history.

(56) References Cited

U.S. PATENT DOCUMENTS

| | | | |
|---|---|---|---|
| 2,608,032 A | 8/1952 | Garver | |
| 2,701,559 A | 2/1955 | Cooper | |
| 2,712,823 A | 7/1955 | Kurtin | |
| 2,867,214 A | 1/1959 | Wilson | |
| 2,881,763 A | 4/1959 | Robbins | |

(Continued)

FOREIGN PATENT DOCUMENTS

| EP | 0258901 | 9/1987 |
|---|---|---|
| EP | 0564392 | 3/1993 |
| EP | 0 564 392 A2 | 10/1993 |

OTHER PUBLICATIONS

File History of Reissue U.S. Appl. No. 11/027,590, filed Dec. 29, 2004 (Reissue of U.S. Patent No. 6,500,183, issued Dec. 31, 2002).

(Continued)

Primary Examiner—Vy Q Bui
(74) Attorney, Agent, or Firm—Knobbe Martens Olson & Bear, LLP

(57) ABSTRACT

An instrument and technique for the removal of epidermal layers in a controlled manner utilizing a hand-held instrument with a working end that (i) a vacuum aspiration system, (ii) a source for delivery of a sterile fluids or pharmacological agents to the skin; and (iii) a skin interface surface in the working end that has specially shape structure for abrading surface layers of the patient's epidermis as the working end is moved over the patient's skin while at the same time causing rapid penetration of the fluids into the skin for therapeutic purposes. Movement of the working end across the skin causes abrasion of the surface layers in a path over the patient's skin. The method of the invention may be used in a periodic treatment for the removal of superficial skin layers that enhances the synthesis of dermal collagen aggregates by inducing the body's natural wound healing response. The method of the invention creates more normal dermal architectures in skin with limited depths of skin removal by the series of superficial treatments that may be comparable to the extent of neocollagenesis caused by a deep skin removal treatment (e.g., $CO^2$ laser skin removal).

9 Claims, 9 Drawing Sheets

U.S. PATENT DOCUMENTS

| | | | |
|---|---|---|---|
| 2,921,585 A | 1/1960 | Schumann | |
| 3,085,573 A | 4/1963 | Meyer et al. | |
| 3,214,869 A | 11/1965 | Stryker | |
| 3,476,112 A | 11/1969 | Elstein | |
| 3,574,239 A | 4/1971 | Sollerud | |
| 3,715,838 A | 2/1973 | Young et al. | |
| 3,964,212 A | 6/1976 | Karden | |
| 4,121,388 A | 10/1978 | Wilson | |
| 4,155,721 A | 5/1979 | Fletcher | |
| 4,182,329 A | 1/1980 | Smith et al. | |
| 4,203,431 A | 5/1980 | Abura et al. | |
| 4,216,233 A | 8/1980 | Stein | |
| 4,378,804 A | 4/1983 | Cortese | |
| 4,560,373 A | 12/1985 | Sugino et al. | |
| 4,646,480 A | 3/1987 | Williams | |
| 4,646,482 A | 3/1987 | Chitjian | |
| 4,676,749 A | 6/1987 | Mabille | |
| 4,706,676 A | 11/1987 | Peck | |
| 4,754,756 A | 7/1988 | Shelanski | |
| 4,757,814 A | 7/1988 | Wang et al. | |
| 4,900,316 A | 2/1990 | Yamamoto | |
| 4,917,086 A | 4/1990 | Feltovich et al. | |
| 4,957,747 A | 9/1990 | Stiefel | |
| 5,012,797 A * | 5/1991 | Liang et al. | 606/131 |
| 5,035,089 A | 7/1991 | Tillman et al. | |
| 5,037,431 A | 8/1991 | Summers et al. | |
| 5,037,432 A * | 8/1991 | Molinari | 606/131 |
| 5,100,412 A | 3/1992 | Rosso | |
| 5,122,153 A | 6/1992 | Harrel | |
| 5,207,234 A | 5/1993 | Rosso | |
| 5,612,797 A | 3/1997 | Clarke | |
| 5,674,235 A * | 10/1997 | Parisi | 606/169 |
| 5,759,185 A | 6/1998 | Grinberg | |
| 5,800,446 A | 9/1998 | Banuchi | |
| 5,810,842 A | 9/1998 | Di Fiore et al. | |
| 5,873,881 A | 2/1999 | McEwen et al. | |
| 5,882,201 A | 3/1999 | Salem | |
| 5,971,999 A | 10/1999 | Naldoni | |
| 6,019,749 A | 2/2000 | Fields et al. | |
| 6,024,733 A | 2/2000 | Eggers et al. | |
| 6,039,745 A | 3/2000 | Di Fiore et al. | |
| 6,042,552 A | 3/2000 | Cornier | |
| 6,080,165 A * | 6/2000 | DeJacma | 606/131 |
| 6,080,166 A | 6/2000 | McEwen et al. | |
| 6,090,085 A | 7/2000 | Mehl, Sr. et al. | |
| 6,136,008 A | 10/2000 | Becker et al. | |
| 6,139,553 A | 10/2000 | Dotan | |
| 6,139,554 A | 10/2000 | Karkar et al. | |
| 6,149,634 A | 11/2000 | Bernabei | |
| 6,162,232 A * | 12/2000 | Shadduck | 606/131 |
| 6,183,483 B1 | 2/2001 | Chang | |
| 6,238,275 B1 | 5/2001 | Metcalf et al. | |
| 6,241,739 B1 | 6/2001 | Waldron | |
| 6,283,978 B1 | 9/2001 | Cheski et al. | |
| 6,299,620 B1 | 10/2001 | Shadduck et al. | |
| 6,306,119 B1 | 10/2001 | Weber et al. | |
| 6,387,103 B2 | 5/2002 | Shadduck | |
| 6,423,078 B1 * | 7/2002 | Bays et al. | 606/131 |
| 6,471,712 B2 | 10/2002 | Burres | |
| 6,500,183 B1 | 12/2002 | Waldron | |
| 6,629,983 B1 | 10/2003 | Ignon | |
| 6,641,591 B1 | 11/2003 | Shadduck | |
| 6,695,853 B2 * | 2/2004 | Karasiuk | 606/131 |
| 6,869,611 B1 * | 3/2005 | Kligman et al. | 424/401 |
| 7,087,063 B2 | 8/2006 | Carson et al. | |
| 2002/0107527 A1 | 8/2002 | Burres | |
| 2003/0212415 A1 | 11/2003 | Karasiuk | |
| 2006/0200172 A1 | 9/2006 | Shadduck | |
| 2006/0200173 A1 | 9/2006 | Shadduck | |

OTHER PUBLICATIONS

File History of Reexamination U.S. Appl. No. 90/007,683 (Reexamination of U.S. Patent No. 6,241,739, issued Jun. 5, 2001).

Ex Parte Reexamination Certificate US 6,241,739 C1, Microdermabrasion Device and Method of Treating the Skin Surface, Inventor Stephen H. Waldron, Dec. 11, 2007, and file history through Aug. 8, 2006.

* cited by examiner

INSTRUMENTS AND TECHNIQUES FOR CONTROLLED REMOVAL OF EPIDERMAL LAYERS

PRIORITY INFORMATION

This application is a continuation of U.S. patent application Ser. No. 10/699,747, filed Nov. 3, 2003, which is a continuation of U.S. patent application Ser. No. 09/648,025 filed Aug. 25, 2000, now U.S. Pat. No. 6,641,591, which claims the priority benefit under 35 U.S.C. §119(e) of Provisional U.S. Patent Application Ser. No. 60/150,782, filed Aug. 26, 1999, the entire contents of these applications being hereby incorporated by reference herein.

BACKGROUND OF THE INVENTION

1. Field of the Invention

The present invention relates to devices for dermatology and more particularly to a hand-held instrument with a working end that carries (i) a negative pressure aspiration system, (ii) a source for delivery of a sterile fluids to the skin; and (iii) a skin interface surface in the working end that has specially shape structure for abrading surface layers of the patient's epidermis as the working end is moved over the patient's skin while at the same time causing rapid penetration of the fluids into the skin for therapeutic purposes.

2. Description of the Related Art

Dermatologists and plastic surgeons have used various methods for removing superficial skin layers to cause the growth of new skin layers (i.e., commonly described as skin resurfacing techniques) since the early 1900's. Early skin resurfacing treatments used an acid such as phenol to etch away surface layers of a patient's skin that contained damage to thereafter be replaced by new skin. (The term damage when referring to a skin disorder is herein defined as any cutaneous defect, e.g., including but not limited to rhytides, hyperpigmentation, acne scars, solar elastosis, other dyschromias, stria distensae, seborrheic dermatitus).

Following the removal of surface skin layers at a particular depth, no matter the method of skin removal, the body's natural wound-healing response begins to regenerate the epidermis and underlying wounded skin layers. The new skin layer will then cytologically and architecturally resemble a younger and more normal skin. The range of resurfacing treatments can be divided generally into three categories based on the depth of the skin removal and wound: (i) superficial exfoliations or peels extending into the epidermis, (ii) medium-depth resurfacing treatments extending into the papillary dermis, and (iii) deep resurfacing treatments that remove tissue to the depth of the reticular dermis (see FIGS. 1A-1B).

Modem techniques for skin layer removal include: $CO_2$ laser resurfacing which falls into the category of a deep resurfacing treatment; Erbium laser resurfacing which generally is considered a medium-depth treatment; mechanical dermabrasion using high-speed abrasive wheels which results in a medium-depth or deep resurfacing treatment; and chemical peels which may range from a superficial to a deep resurfacing treatment, depending on the treatment parameters. A recent treatment, generally called micro-dermabrasion, has been developed that uses an air-pressure source to deliver abrasive particles directly against a patient's skin at high-velocities to abrade away skin layers. Such a micro-dermabrasion modality may be likened to sandblasting albeit at velocities that do no cause excess pain and discomfort to the patient. Micro-dermabrasion as currently practiced falls into the category of a superficial resurfacing treatment.

A superficial exfoliation, peel or abrasion removes some or all of the epidermis (see FIGS. 1A-1B) and thus is suited for treating very light rhytides. Such a superficial exfoliation is not effective in treating many forms of damage to skin. A medium-depth resurfacing treatment that extends into the papillary dermis (see FIG. 1B) can treat many types of damage to skin. Deep resurfacing treatments, such as $CO_2$ laser treatments, that extend well into the reticular dermis (see FIG. 1B) causes the most significant growth of new skin layers but carry the risk of scarring unless carefully controlled.

It is useful to briefly explain the body's mechanism of actually resurfacing skin in response to the removal of a significant depth of dermal layers. Each of the above-listed depths of treatment disrupts the epidermal barrier, or a deeper dermal barrier (papillary or reticular), which initiates varied levels of the body's wound-healing response. A superficial skin layer removal typically causes a limited wound-healing response, including a transient inflammatory response and limited collagen synthesis within the dermis. In a medium-depth or a deep treatment, the initial inflammatory stage leads to hemostasis through an activated coagulation cascade. Chemotactic factors and fibrin lysis products cause neutrophils and monocytes to appear at the site of the wound. The neutrophils sterilize the wound site and the monocytes convert to macrophages and elaborate growth factors which initiate the next phase of the body's wound-healing response involving granular tissue formation. In this phase, fibroblasts generate a new extracellular matrix, particularly in the papillary and reticuilar dermis, which is sustained by angiogenesis and protected anteriorly by the reforming epithelial layer. The new extracellular matrix is largely composed of collagen fibers (particularly Types I and III) which are laid down in compact parallel arrays (see FIG. 1B). It is largely the collagen fibers that provide the structural integrity of the new skin—and contribute to the appearance of youthful skin.

All of the prevalent types of skin damage (rhytides, solar elastosis effects, hyperpigmentation, acne scars, dyschromias, melasma, stria distensae) manifest common histologic and ultrastructural characteristics, which in particular include disorganized and thinner collagen aggregates, abnormalities in elastic fibers, and abnormal fibroblasts, melanocytes and keratinocytes that disrupt the normal architecture of the dermal layers. It is well recognized that there will be a clinical improvement in the condition and appearance of a patient's skin when a more normal architecture is regenerated by the body's wound-healing response. Of most significance to a clinical improvement is skin is the creation of more dense parallel collagen aggregates with decreased periodicity (spacing between fibrils). The body's wound-healing response is responsible for synthesis of these collagen aggregates. In addition to the body's natural wound healing response, adjunct pharmaceutical treatments that are administered concurrent with, or following, a skin exfoliations can enhance the development of collagen aggregates to provide a more normal dermal architecture in the skin—the result being a more youthful appearing skin.

The deeper skin resurfacing treatments, such as laser ablation, chemical peels and mechanical dermabrasion have drawbacks. The treatments are best used for treatments of a patient's face and may not be suited for treating other portions of a patient's body. For example, laser resurfacing of a patient's neck or decolletage may result in post-treatment pigmentation disorders. All the deep resurfacing treatments are expensive, require anesthetics, and must be performed in a clinical setting. Perhaps, the most significant disadvantage to deep resurfacing treatments relates to the post-treatment recovery period. It may require up to several weeks or even months to fully recover and to allow the skin the form a new epidermal layer. During a period ranging from a few weeks to several weeks after a deep resurfacing treatment, the patient typically must wear heavy make-up to cover redness thus making the treatment acceptable only to women.

The superficial treatment offered by micro-dermabrasion has the advantages of being performed without anesthetics and requiring no extended post-treatment recovery period. However, micro-dermabrasion as currently practices also has several disadvantages. First, a micro-dermabrasion treatment is adapted only for a superficial exfoliation of a patient's epidermis which does not treat many forms of damage to skin. Further, the current micro-dermabrasion devices cause abrasive effects in a focused area of the skin that is very small, for example a few mm.sup.2, since all current devices use a single pin-hole orifice that jets air and abrasives to strike the skin in a highly focused area. Such a focused treatment area is suitable for superficial exfoliations when the working end of the device is passed over the skin in overlapping paths. Further, such focused energy delivery is not well suited for deeper skin removal where repeated passes may be necessary. Still further, current micro-dermabrasion devices are not suited for deeper skin removal due to the pain associated with deep abrasions. Other disadvantages of the current micro-dermabrasion devices relate to the aluminum oxide abrasive particles that are typically used. Aluminum oxide can contaminate the working environment and create a health hazard for operators and patients alike. Inhalation of aluminum oxide particles over time can result in serious respiratory disorders.

DETAILED DESCRIPTION OF THE PREFERRED EMBODIMENTS

Figure 1A:
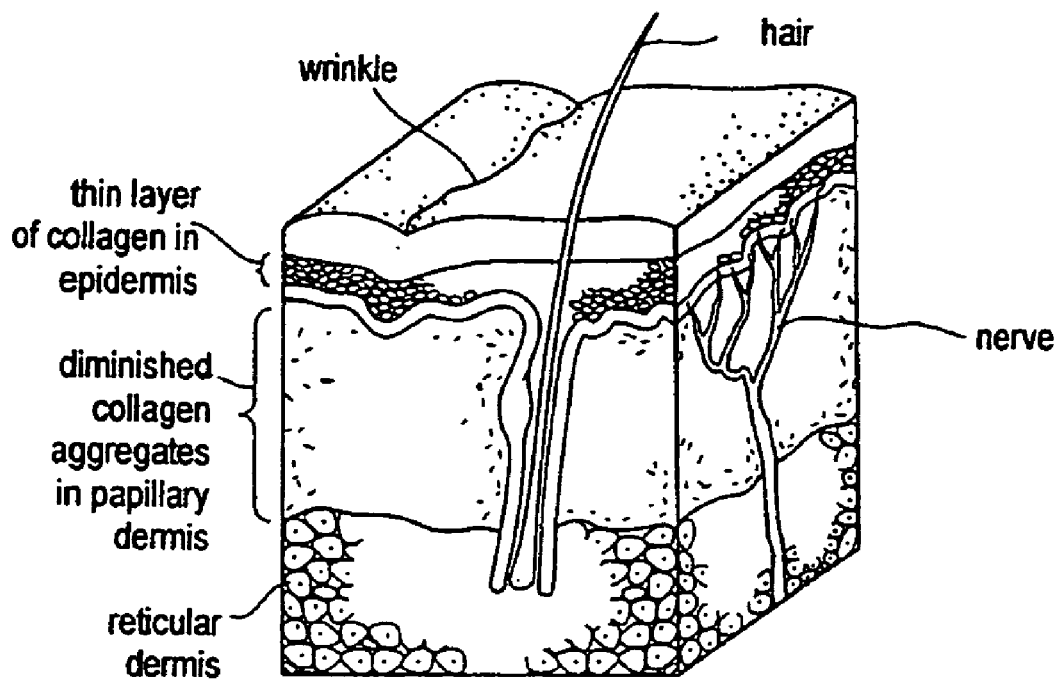
FIGS. 1A-1B are sectional illustrations of a patient's skin showing dermal layers.
Figure 1B:
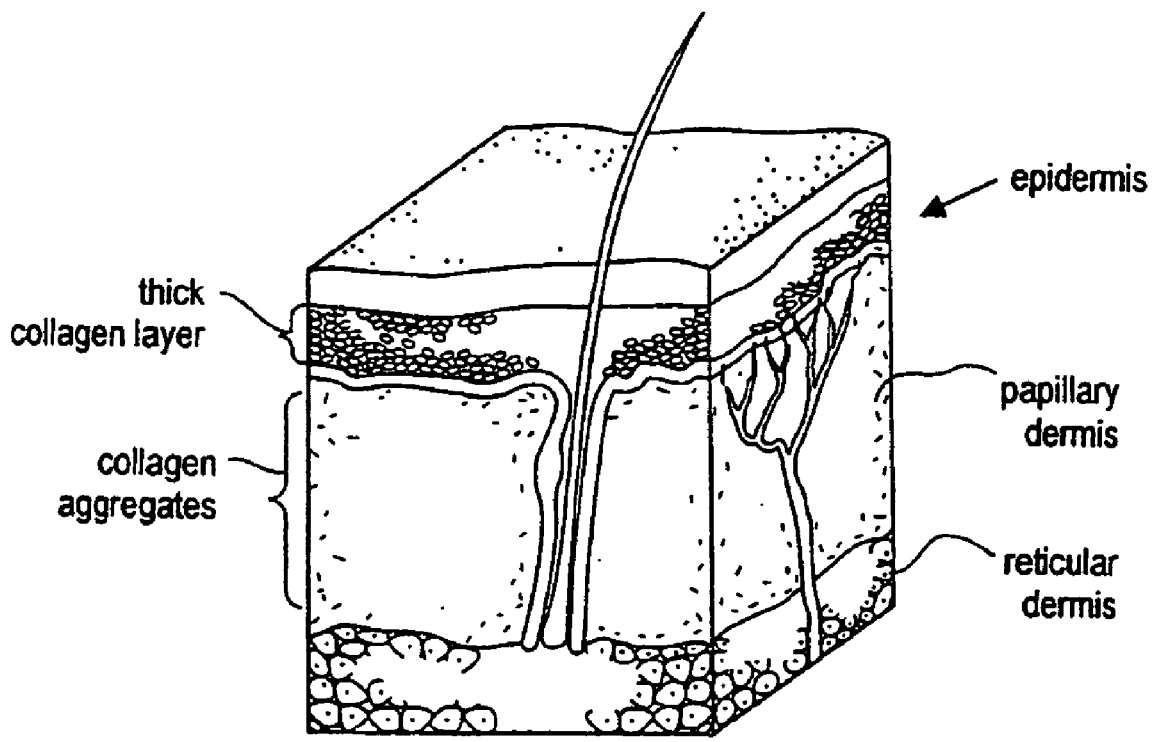
Figure 2:
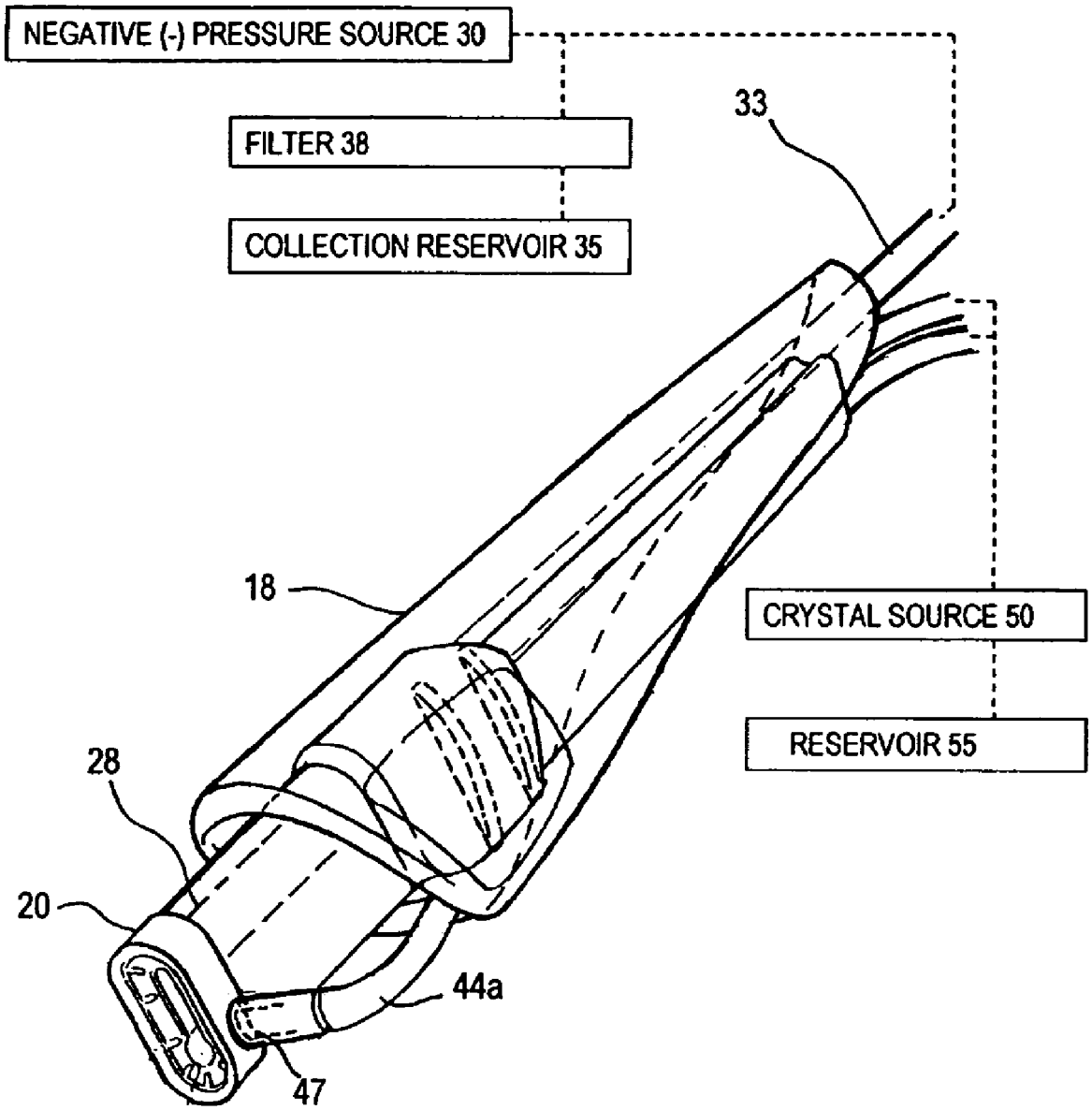
FIG. 2 is a view of a Type "A" body and working end of the instrument of the invention.
Figure 3:
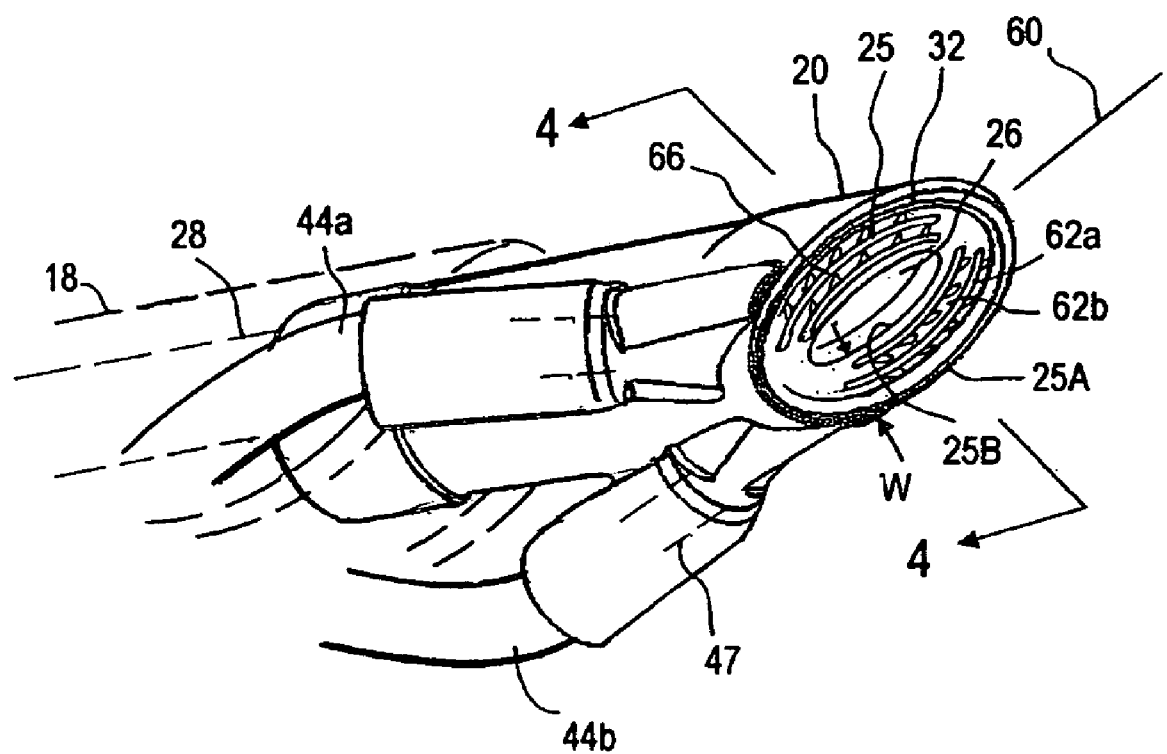
FIG. 3 is an enlarged view of the working end of the instrument of FIG. 2.

1. Type "A" Skin Resurfacing System. Referring to FIGS. 2-3, an exemplary instrument system 5 is shown for removing superficial skin layers. The instrument system 5 includes: (i) a hand-held body 18 with a working end 20 that defines a skin interface surface portion indicated at 25 in FIGS. 2-3. An opening portion 26 transitions into an interior passageway 28 that extends through the body to communicate with a negative (−) pressure source (or aspiration source) indicated at 30 that operates as vacuum means for aspirating skin debris from a targeted skin surface treatment site TS.

Figure 4:
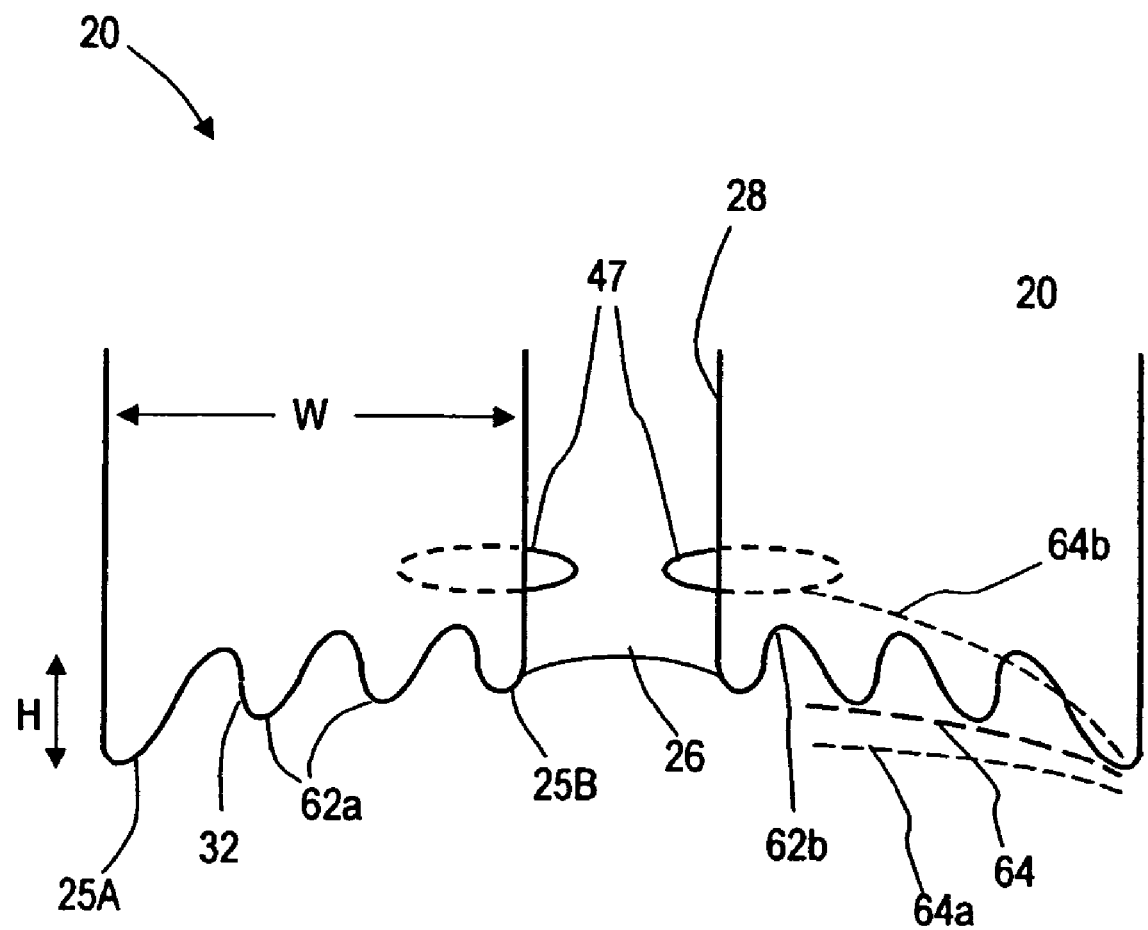
FIG. 4 is a sectional view of working end of FIG. 3.

Of particular interest, FIGS. 3-4 show views of the working end 20 with the skin interface 25 being configured with a particular irregular or ridged surface structure indicated at 32. The ridged surface structure 32 further has a particular minimum width dimension W to accommodate from the ridge shape with as many as about 25 ridges on each side of opening 26 depending on the overall dimensions of the working end 20. More particular aspects of the irregular or ridged surface structure 32 will be described below.

In this preferred embodiment, the working end 20 is of any suitable material, such as a transparent medical grade plastic. The transparency of the working end will assist the operator in localizing treatment in a particular targeted skin treatment area. The overall transverse dimension of the working end 20 of FIGS. 2-3 may be from around about 5.0 mm. to about 50.0 mm. with a larger dimensioned end being adapted for treating a larger skin area (e.g., arms, back legs and decolletage). A typical dimension is from about 5.0 mm. to 15.0 mm. for a skin treatment site area TS around a patient's face.

The invention allows the area (e.g., in $mm^2$) of opening 26 be in any selected shape but preferably is an elongate shape in the center of the working end 25. The open distal end 26 comprises the distal termination of passageway 28 and the proximal end of the passageway in handle 18 is connected to a flexible aspiration tube 33 that extends to a remote collection reservoir 35 intermediate to the actual aspiration source 30. The aspiration source 30 thus is adapted to draw the working end 20 and more particularly the skin interface 25 against the skin treatment site TS to perform the method of the invention as will be described below. The aspiration source or negative (−) pressurization source 30 may be any suitable vacuum source known in the art. Between the aspiration source 30 and remote collection reservoir 35 may be a filter 38 subsystem that is known in the art for collecting aspirated skin detritus and spent crystalline agents CA that are captured in the open distal end of passageway chamber 28. The collection reservoir 35 and filter 38 are preferably of inexpensive plastic and other materials that are disposable.

The aspiration source 30 may be provided with an adjustable valve means 40 for adjusting the pressure level setting to any suitable range. The physician will learn from experience how to balance the pressure level to attain the desired level of suction against the patient's skin. A trigger or switch component 42 is provided as a foot-switch (FIG. 2) but any suitable finger switch in the body 18 also may be used.

The working end 20 also carries means for introducing abrasive crystals into the working end or distalmost end of passageway 28 to allow individual loose crystalline agents CA to thereafter be captured between the skin interface 25 and the patient's skin. In this embodiment, two channels 44a-44b are provided together with flexible tubes 46a-46b to introduce the loose crystalline agents CA into the working end (see FIGS. 2-4). Each distal portion 47 (collectively) of the channels 44a-44b may comprise a small dimension aperture to limit the rate of flow of crystalline agents CA into the working end. The number of such channels (i.e., 44a-44n) may range from one to about ten and fall within the scope of the invention. Any singular or plural number of channels can serve the purpose of slowly introducing crystal into the working end. Referring to FIGS. 2-3, the crystalline agent CA delivery source 50 comprises a reservoir 55 that holds a suitable volume of abrasive crystals for a single treatment or a number of treatments. A flexible supply tube 56 extends between a remote the reservoir 55, and in this embodiment the tube is split to connect to the two channels 44a-44b. Preferably, the remote reservoir 55 that carries the crystalline agent CA is unpressurized but carries air intake relief valve 58 such that any slight negative pressure created by the aspiration source 30 when the skin interface is in contact with a patient's skin will draw crystals to the working end. It should be appreciated that reservoir 55 may be built into handle body 18 and fall within the scope of the invention. The crystal delivery source 50 may carry crystals ranging in size from about 1 µm to about 50 µm in maximum cross-sectional dimension, (for example, aluminum oxide crystals). Preferably, the crystals are from about 5 µm to about 30 µm in maximum cross-sectional dimension to allow a very fine abrasion of the epidermis.

It has been found that by a slight negative pressure environment the open end 26 and passageway 28, the crystalline agent will be caused to dribble into, or be sucked into, the passageway 28 in the working end 20. Thereafter, the movement of the working end 20 in a sideways movement over the skin causes a portion of the crystalline agent CA volume to be captured temporarily in the irregular or corrugated surface structure of the skin interface 25. In this process of moving the skin interface 25 over the targeted treatment site TS, it has been found that the sharp-edged crystalline agents are rolled over and over while being pressed into the surface of the skin and thereby abrade and remove the skin surface in a controllably gentle manner that is below any threshold of significant pain.

After the spent crystals are rolled over and over by the skin interface when moving in a first lateral direction across the skin, and after the working end is then is reversed in directional movement across the skin, a portion of the spent crystals and abraded skin debris necessarily roll into the central opening portion 26 wherein the negative pressure environment captures and aspirates the abraded materials to the remote collection reservoir 35.

To facilitate the process described above, the invention is provided with novel aspects that relate to the irregular or ridged surface structure 32 mentioned above. The entire skin interface 25 may be of any suitable plan form (e.g., round, oval, rectangular etc.) and fall within the scope of the invention. More in particular, the interface 25 defines a $1^{st}$ outer periphery 25A and a $2^{nd}$ inner periphery 25B that generally are in apposition to one another and are spaced apart by width W with the inner periphery about the edge of opening 26 (see FIG. 3).

In a preferred embodiment shown in FIGS. 3-4, the concept of $1^{st}$ and $2^{nd}$ peripheries 25A and 25B in apposition thus comprise peripheries that are dual and side-by-side as shown in FIG. 4 and are thus adapted for side-to-side lateral or sideways movement while performing the technique of the invention, for example which is a natural movement of a human hand over a patient's skin. Thus, the direction of the ridges 60 extend generally transverse relative to a line drawn that indicates the direction of movement of the working end 20 in performing the method of the invention. That is, in the exemplary working end of FIG. 4, the working end is generally optimized for side-to-side or lateral movement. Thus, the ridge alignment is generally transverse to the direction of movement in operations indicated by arrow A. (In a circular working end that is adapted generally for movement is any direction, the direction of the ridges 60 may be generally transverse to any direction of movement by being concentric relative to a central opening 26 (not shown)).

The terms irregular or ridged shape structure 32 as used herein mean that a series of at least one projecting edge portion 62a projects distally as a ridge within the skin interface portion 25. The irregular shape structure 32 further typically carries recessed portions or valley portions 62b that are recessed in the proximal direction intermediate to any plurality of projecting edge portions 62a. These surface configurations for convenience are herein termed the primary shape structure (or ridge and valley elements). The width of the skin interface 25 containing shape structure 32 may be from about 2.0 mm. to 25.0 mm. or more and preferably is from about 3.0 mm. to 10.0 mm. The number of ridges preferably are from about 1 ridge to 25 ridges on each side of the opening 26. The height H of any ridge from the apex of the projecting portion 62a to the depth of the valley portion 62b may be from about 0.25 mm. to about 5.0 mm. and is preferably from about 0.5 mm. to about 2.0 m. It has been found that various ridge height dimensions are optimal depending on the patient's skin type. Further, but optionally, it has been found that secondary shape structure of notches or recessed grooves 66 configured across the primary shape structure of ridge and valley elements may help introduce loose crystals to regions of the skin interface 25 in contact with the skin which is desirable. Such secondary grooves 66 are shown in FIG. 4 and are preferably somewhat in alignment with an axis of channels 44a-44b that introduce crystals into the working end 20 thus allowing the crystals to be suctioned into the valleys 62b of the primary shape structure.

While the series of primary ridge and valley elements together the secondary grooves seems to be optimal for the method described below, it should be appreciated that the method also may be performed with a skin interface that has (i) only primary ridge and valley elements; (ii) or only a particular surface roughness that is appropriate for partially capturing loose crystals as will be described below-as long as the skin interface has a minimum width of about 3.0 mm. which was described as a preferred width dimension previously.

FIG. 4 further shows that at least some of the crests or apexes of some of the ridge portions 62a together with the outermost periphery of the skin interface 25 define an overall tissue-receiving shape 64 that may range from flat to concave and is shown in a preferred concave configuration. The alternative shapes 64a-44b are intended to indicate an approximate range of shapes that are suitable. The apexes of ridges 62a need not all be at the same height to define shape 64. The purpose of the concave shape is to cause the outer periphery of the working end to be in firm contact with the tissue surface while the negative pressure from aspiration source 30 draws the skin into firm contact with tissue interface 25.

Figure 5:
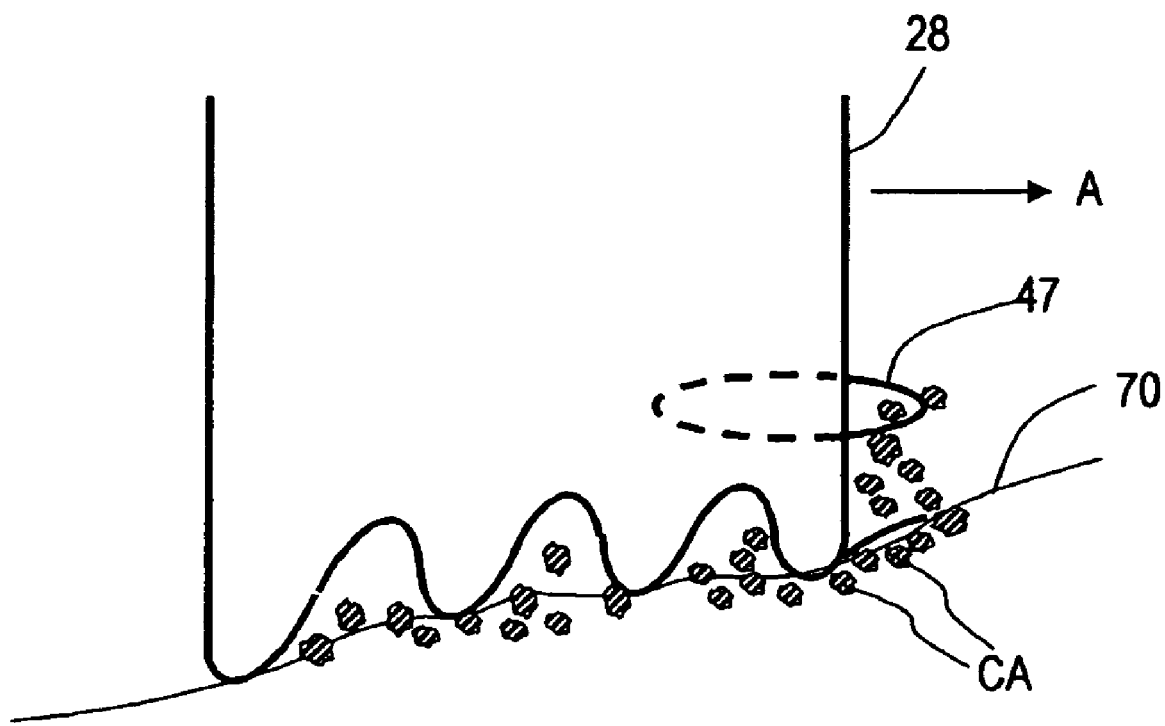
FIG. 5 is a view showing the manner of using the working end of the invention of FIGS. 3-4 in performing a method of the invention.

2. Practice of the Method of the Invention. Now turning to FIG. 5, a sectional view of working end 20 shows the technique of the present invention in exfoliating or removing skin surface layers. FIG. 5 shows the working end 20 after actuation of the negative (−) pressure source 30 with the skin surface 70 initially being drawn into the concave shape 64. The operating negative pressures may be in any suitable range that is determined by investigation. It has been found by experimentation that optimal pressure levels vary greatly depending on (i) the type of skin targeted for treatment, (ii) the dimensions across the working end, and (iii) the dimensions of opening 26.

Next, the operator moves the skin interface 25 across a treatment site TS which is a path on the patient's skin while still actuating moves the trigger 42 thereby maintaining the negative pressure environment in the passageway 26. The negative pressure environment within the working end causes crystalline particles and entrained in air to be drawn into passageway 28 proximate to the skin surface and into the shape structure 32 of the skin interface 25. The sideways or lateral movement of the skin interface 25 captures a portion of the crystals between the interface and the skin surface, in part by over-rolling them. The continued rolling of the sharp-edged crystals trapped between the instrument and the skin surface 70 causes an abrasion and removal of the skin surface in a controllable manner.

As working end is moved in a reverse direction, the negative pressure environment in the passageway 28 captures and aspirates the spent crystals and skin debris to the remote collection reservoir 35. At the end of a particular lateral movement of the working end, the operator may release the trigger 42 which terminates the crystal agent delivery and further allows the operator to easily lift the working end from the patient's skin. The treated path can be easily seen and the operator then can exfoliate another slightly overlapping or adjacent path by repeating the above steps until surface removal is completed over the targeted treatment area.

3. Type "B" Skin Resurfacing System. Referring to FIGS. 6-9, another exemplary instrument system and treatment device 205 is shown for removing superficial skin layers. This system differs greatly from the Type "A" embodiment in the mechanism of action that abrades the skin since the Type "B" system uses a fluid media plus an abrading structure on the skin interface. Still several features of the Type "B" embodiment are similar to the Type "A" embodiment and the two modalities of treatment may be used to complement one another.

Figure 6:
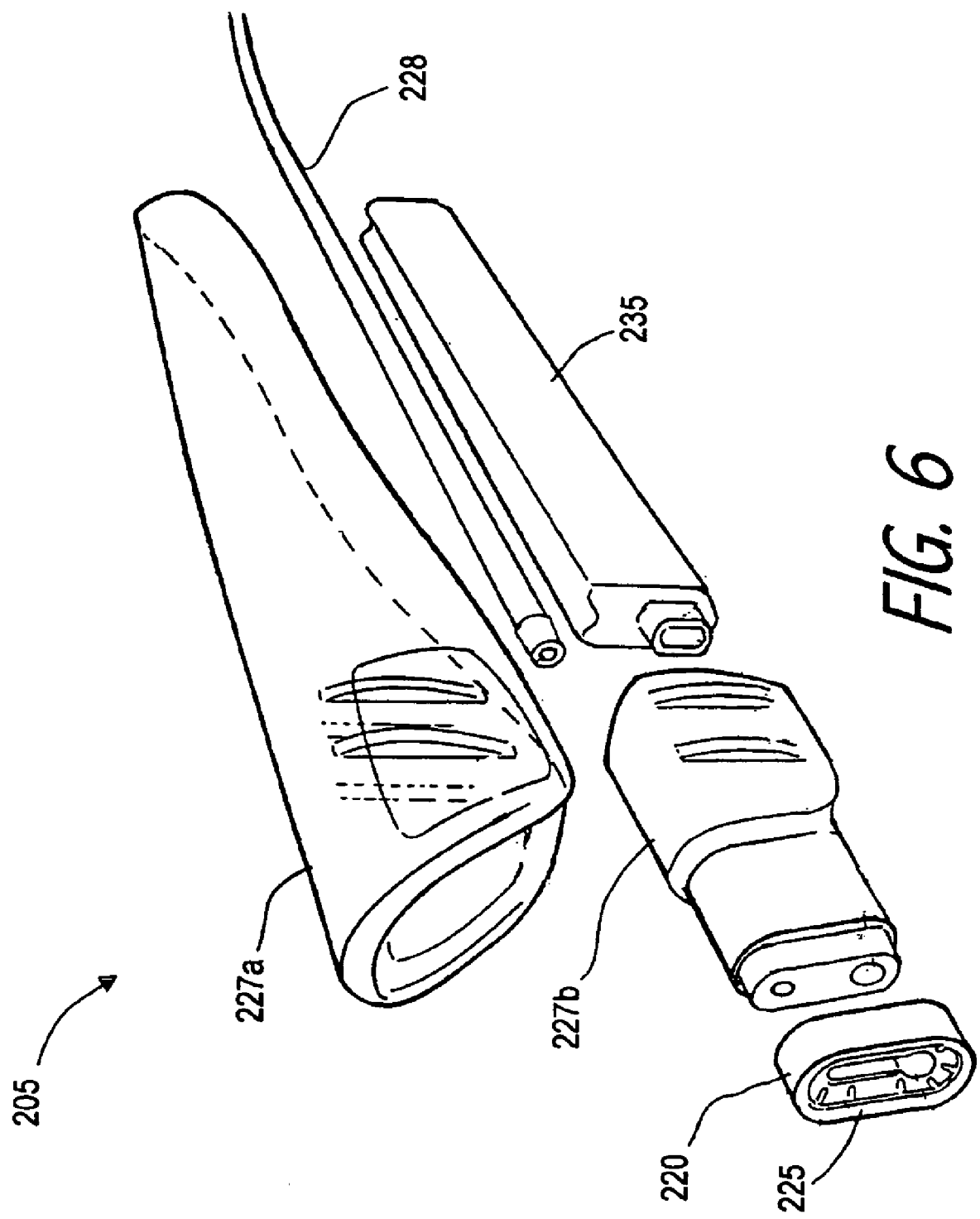
FIG. 6 is a view of a Type "B" body, working end and handle in an exploded view.

FIG. 6 shows that a hand-held instrument 208 has a removable working end 220 that defines a skin interface surface portion indicated at 225. Handle portion 227a mates with housing 227b. A flexible tube 228 extends to a vacuum source 230. A fluid reservoir 235 carrying a fluid skin treatment media is housed in the handle although it could also be a remote reservoir.

Figure 7:
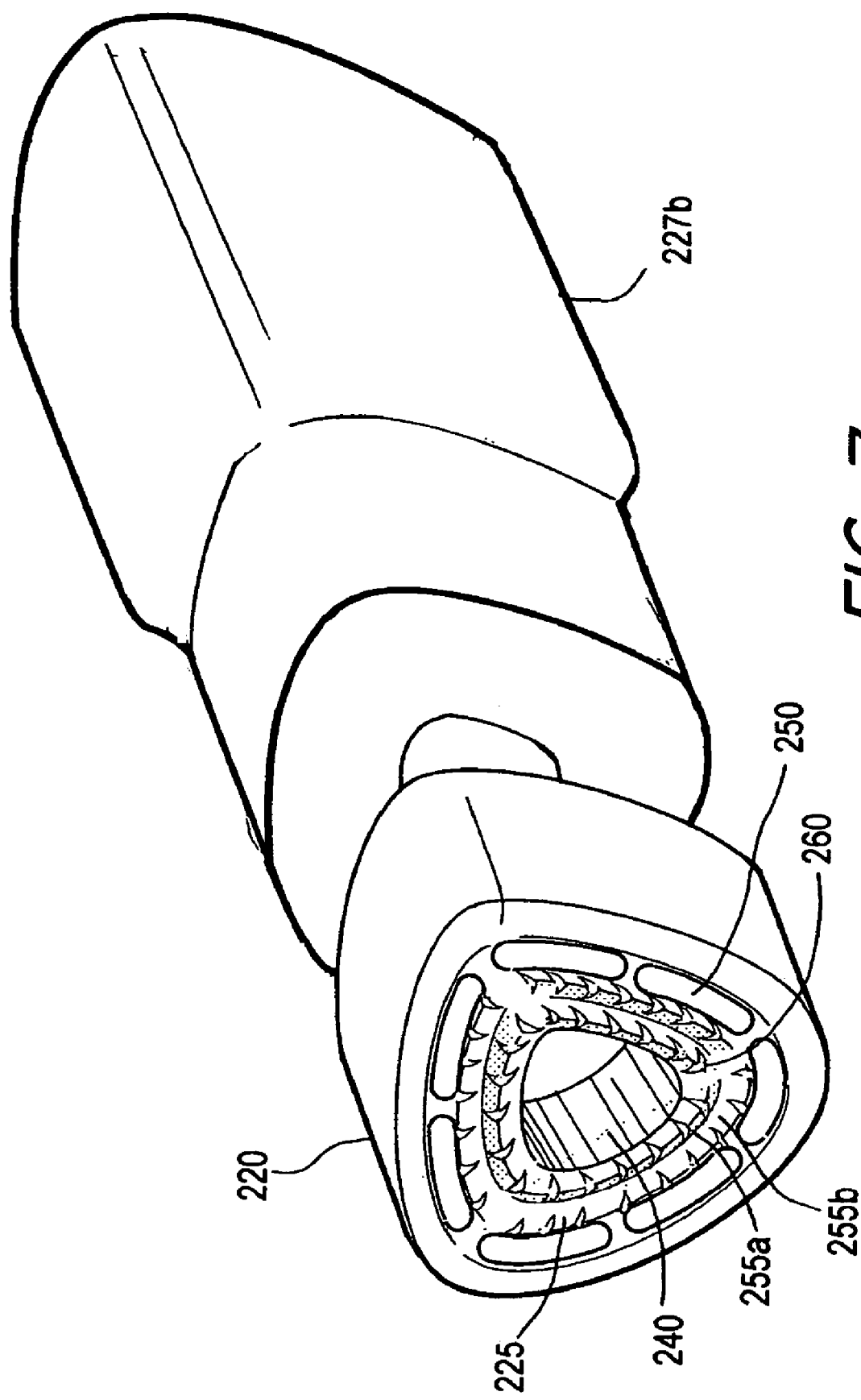
FIG. 7 is a view of the working end of the instrument of FIG. 6 and a housing.
Figure 8:
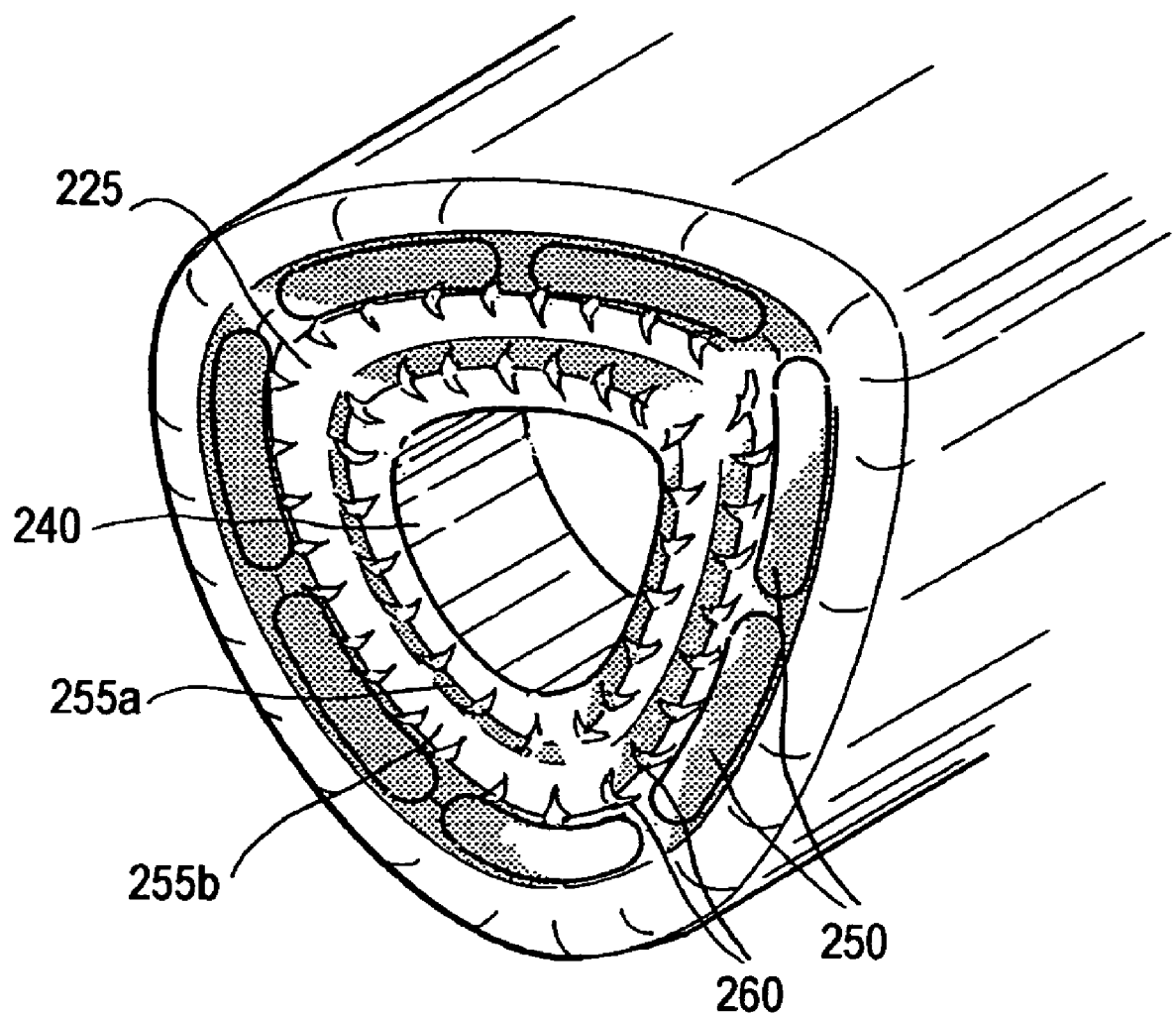
FIG. 8 is an enlarged view of the skin interface of the working end of FIG. 7.
Figure 9:
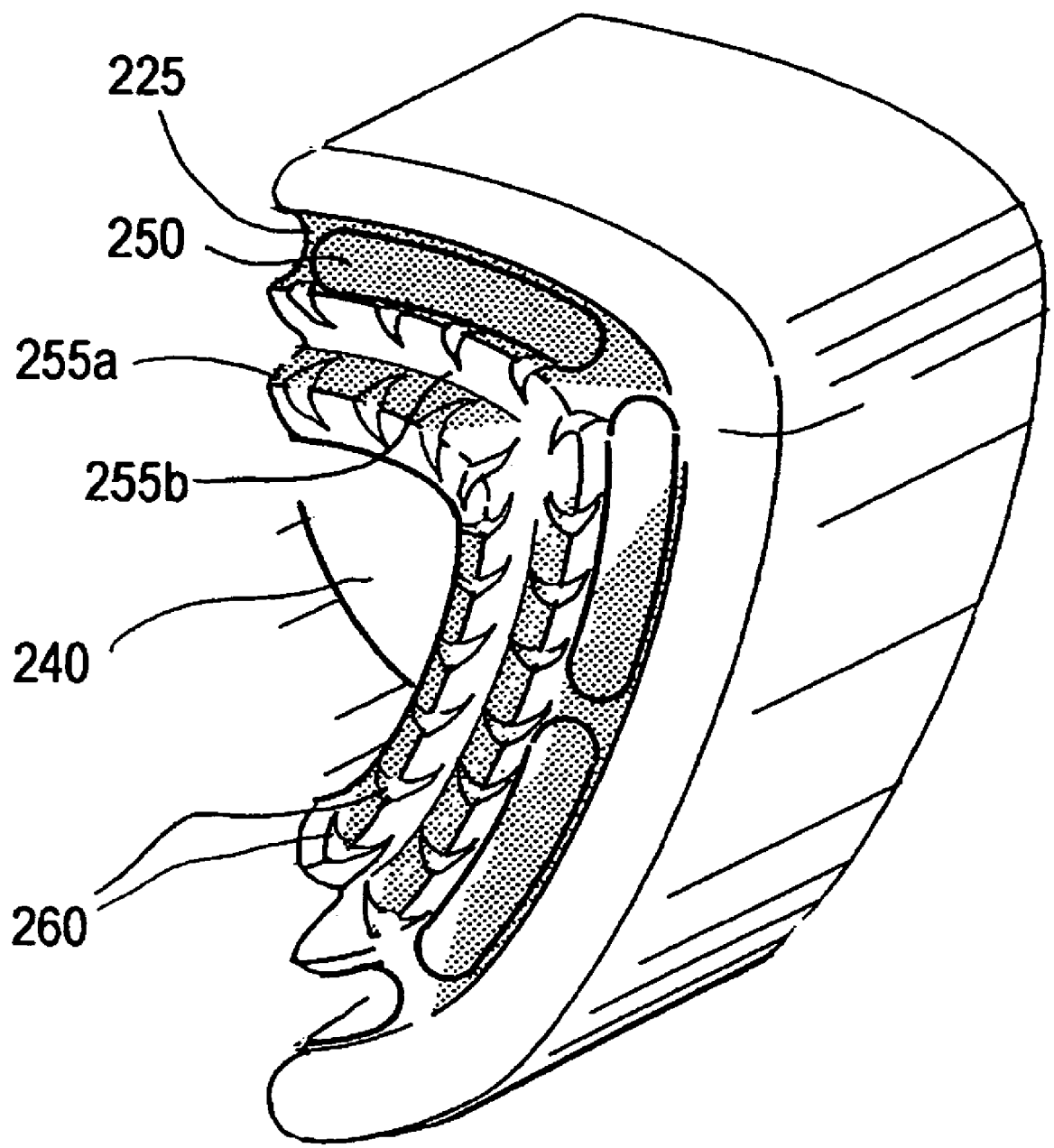
FIG. 9 is a sectional view of the skin interface of FIG. 8.

Referring now to FIGS. 7-9, a first aperture arrangement consisting of at least one port or opening portion 240 of skin interface 225 that communicates with an interior passageway 242 that extends through housing 227b to hose 228 and the vacuum or negative (−) pressure source.

FIGS. 7-9 further show a second aperture arrangement in the skin interface consisting of at least one port or openings 250 that extend around an outer periphery of the skin interface 225. These opening(s) of the second aperture arrangement are in fluid communication with the reservoir 235 and the treatment media therein. The skin interface has a series of primary ridge elements 255a and valley elements 255b together the secondary notches or grooves 260 as defined above with similar dimensional parameters. This embodiment differs however in that the apexes of ridge elements 255a are substantially a sharp edge as are the edged of the notches 260. Thus, these primary surface elements 255a and secondary surface elements thereby define teeth therebetween that seem well suited to abrading skin layers particularly after being hydrated by the fluid source of the system. Experimentation has shown that the vacuum source and fluid source may be reversed between the first and second aperture arrangements 240 and 250 with the method of skin removal still working well. The vacuum system aspirates away skin debris and spent fluids as described previously. Of particular interest, the method of the invention appears to work well because the suction on the skin treatment site very quickly hydrated, or puffs up, the skin which in turn make the surface layer susceptible to painless abrasion. The ability of the system to rapidly deliver fluids to subsurface tissues allows the use of any pharmacological agent known in the art for enhancing skin rejuvenation as a part of the skin treatment. The system can use sterile water or saline solution for a treatment to remove dermal tissue with the abrasive surface of the treatment device. The system can also use a fluid carrying a chemical agent of a suitable concentration be selected from a group of acids including TCA (trichloroacetic acid), a glycolic acid including an alphahydroxy acid (AHA), a lactic acid, a citric acid, or phenol as disclosed in co-pending U.S. patent application Ser. No. 09/524,731 filed Mar. 14, 2000 which is incorporated herein by this reference.

Specific features of the invention may be shown in some figures and not in others, and this is for convenience only and any feature may be combined with another in accordance with the invention. While the principles of the invention have been made clear in the exemplary embodiments, it will be obvious to those skilled in the art that modifications of the structure, arrangement, proportions, elements, and materials may be utilized in the practice of the invention, and otherwise, which are particularly adapted to specific environments and operative requirements without departing from the principles of the invention. The appended claims are intended to cover and embrace any and all such modifications, with the limits only of the true purview, spirit and scope of the invention.

What is claimed is:

1. A method for abrading skin of a patient, comprising:
   (a) placing a working end of a skin treatment device against the skin of the patient;
   (b) drawing the skin against an abrading surface on a skin interface on the working end of the skin treatment device by applying suction to the skin through an aspiration opening in the working end, the abrading surface comprising apexes extending upwardly from the abrading surface and the apexes having sharp edges;
   (c) moving the treatment device across the skin while the sharp edge of the apexes remain stationary with respect to the working end of the skin treatment device;
   (d) abrading the skin drawn against the sharp edge of the apexes while continuously applying suction through the aspiration opening; and
   (e) removing skin debris through the aspiration opening in the working end of the skin treatment device.

2. The method of claim 1, further comprising providing a fluid to the skin.

3. The method of claim 2, wherein the fluid is provided with a crystalline abrasive.

4. The method of claim 2, wherein the fluid hydrates the skin.

5. The method of claim 2, wherein the fluid is provided with a pharmacologically-active agent for treating skin.

6. The method of claim 2, wherein the fluid is provided with an agent selected from the class consisting of citric acid and lactic acid.

7. The method of claim 2, wherein the fluid is provided with an agent selected from the class comprising TCA (trichloroacetic acid), glycolic acid, alphahydroxy acid (AHA).

8. The method of claim 3, wherein providing a fluid to the skin the fluid further comprises providing through a fluid opening provided in the working end of the skin treatment device.

9. The method of claim 2, further comprising providing sterile water or saline solution to the skin.

* * * * *